United States Patent [19]
Santus et al.

[11] Patent Number: 5,510,119
[45] Date of Patent: *Apr. 23, 1996

[54] CONTROLLED RELEASE THERAPEUTIC SYSTEM FOR LIQUID PHARMACEUTICAL FORMULATIONS

[75] Inventors: Giancarlo Santus, Milan; Roberto Golzi, Cremona, both of Italy

[73] Assignee: Recordati S.A., Chemical and Pharmaceuticl Company, Chiasso, Switzerland

[*] Notice: the term of this patent shall not extend beyond the expiration date of Pat. No. 5,296,236.

[21] Appl. No.: 394,660

[22] Filed: Feb. 22, 1995

Related U.S. Application Data

[63] Continuation of Ser. No. 191,013, Feb. 1, 1994, Pat. No. 5,405,619, which is a continuation of Ser. No. 928,616, Aug. 10, 1992, Pat. No. 5,296,236, which is a continuation of Ser. No. 711,588, Jun. 6, 1991, abandoned, which is a continuation of Ser. No. 408,755, Sep. 18, 1989, abandoned.

[30] Foreign Application Priority Data

Sep. 16, 1988 [IT] Italy ........................ 21961/88

[51] Int. Cl.$^6$ .................................... A61K 9/16
[52] U.S. Cl. .............. 424/490; 424/493; 424/494; 424/495; 424/498
[58] Field of Search .................. 424/490, 493–495, 424/498

[56] References Cited

U.S. PATENT DOCUMENTS

| | | | |
|---|---|---|---|
| 2,921,883 | 1/1960 | Reese | 167/82 |
| 4,193,985 | 3/1980 | Bechgaard | 424/19 |
| 4,572,833 | 2/1986 | Pedersen | 424/20 |
| 4,728,512 | 3/1988 | Mehta | 424/458 |
| 4,780,312 | 10/1988 | Appelgren | 424/469 |
| 4,820,521 | 4/1989 | Panoz | 424/458 |
| 4,828,840 | 5/1989 | Sakamoto | 424/474 |
| 4,876,094 | 10/1989 | Benton | 424/491 |
| 4,935,247 | 6/1990 | Marttila | 424/494 |
| 5,133,947 | 7/1992 | Paradissis | 424/480 |
| 5,178,868 | 1/1993 | Malmquist-Granlund | 424/490 |

FOREIGN PATENT DOCUMENTS

| | | |
|---|---|---|
| 1468172 | 3/1977 | United Kingdom. |
| 2166651 | 5/1986 | United Kingdom. |
| 8503000 | 7/1985 | WIPO. |
| 8707833 | 12/1987 | WIPO. |
| 8802253 | 4/1988 | WIPO. |

OTHER PUBLICATIONS

W. P. O'Neill, Chapter 4, Controlled Release Technologies: Methods, Theory and Applications, Kydonieus (ed), CRC Press, Inc., Boca Raton, Florida (1980).

*Primary Examiner*—D. Gabrielle Phelan
*Attorney, Agent, or Firm*—Darby & Darby

[57] ABSTRACT

Disclosed is a controlled release pharmaceutical dosage form, including: (a) microgranules of a pharmaceutical and an excipient; (b) a plurality of polymeric lipidic and wax-like coatings applied to the microgranules, the coated microgranules having dimensions which allow suspension of the coated microgranules in a liquid administration vehicle; and (c) a liquid administration vehicle for the coated microgranules, the vehicle including an effective amount of the pharmaceutical in a form immediately available upon ingestion. A process for the preparation of the controlled release therapeutic system is also described.

3 Claims, No Drawings

CONTROLLED RELEASE THERAPEUTIC SYSTEM FOR LIQUID PHARMACEUTICAL FORMULATIONS

This is a continuation of application Ser. No. 08/191,013, filed Feb. 11, 1994 issued as U.S. Pat. No. 5,405,619, which is a continuation of Ser. No. 07/928,616, filed Aug. 10, 1992 issued as U.S. Pat. No. 5,296,236, which is a continuation of Ser. No. 07/711,588, filed Jun. 6, 1991, now abandoned, which is a continuation of Ser. No. 408,755, filed Sep. 18, 1989, now abandoned.

FIELD OF THE INVENTION

The present invention is directed to controlled release therapeutic systems. More particularly, the present invention is directed to controlled release therapeutic systems for liquid pharmaceutical formulations.

BACKGROUND OF THE INVENTION

An important aspect of the administration of drugs in conventional forms is the fluctuation between high and low plasma concentration of the drug in the period between the administration of two successive doses. In fact, if the drug is too rapidly absorbed, excessive plasma levels may be attained, leading to undesirable and even toxic side effects. On the other hand, drugs possessing a short half-life are eliminated too rapidly and require therefore frequent administrations. In both cases the patient must be careful because particular attention and constancy in the administration is required during therapy and such conditions can not always be easily obtained. Many efforts have been made to formulate pharmaceutical preparations able to protract in time the activity of the drug in the body at optimum plasma levels, reducing the number of administrations and thus improving the response of the patient to the treatment.

The preparation of pharmaceutical compositions intended to supply a gradual and controlled release in time of the active ingredient is well known in the pharmaceutical technology field. Systems are known comprising tablets, capsules, microcapsules, microspheres and formulations in general in which the active ingredient is released gradually by various means.

It is also known that oral administration is by far the most frequently employed in therapy and the most appreciated by the patient, particularly when repeated administrations are otherwise necessary. Among formulations for oral administration, the liquid ones present the advantage of being easily adaptable to the patient in dosage and better accepted by the patient, particularly by children and the elderly. For this reason a liquid controlled release formulation is more advantageous compared to a corresponding controlled release solid formulation.

In the preparation of controlled release liquid pharmaceutical compositions several problems may be encountered. One problem is that the actual controlled release forms must be of such a size to be easily suspended and kept in suspension in the liquid vehicle. Furthermore, poor or non-homogeneous distribution in the vehicle is to be avoided as far as possible, and it is also preferable to avoid the unpleasant sensation which may be present upon ingestion of a suspension containing a solid of coarse particles (sand effect). This problem may be avoided by suitably reducing the size of the particles to be suspended. On the other hand, the use of reduced size particles, increasing the surface area available for diffusion, makes it difficult to obtain a constant and protracted control of release, as is possible with particles having larger dimensions.

A further problem is the difficulty of obtaining controlled release liquid preparations able to maintain for a long period the release characteristics of the pharmaceutical compound contained. The solution of these problems is commercially and therapeutically important both for the necessity of having ready-to-use liquid dosage formulations as far as possible stable in time, and for having liquid formulations which, prepared at the moment of use, will remain stable for a long time once the dispersion of the therapeutic agent in the dosage liquid has taken place.

All the above mentioned difficulties may explain why only a few controlled release liquid systems are known, and among them only one is actually available commercially. Examples of known controlled release liquid formulations are found in the following patents: BE903540, WO85/03000, WO 87/07833, U.S. Pat. No. 4,221,778 and U.S. Pat. No. 4,717,713.

The necessity is felt therefore, for a system which allows the administration of substances in a liquid oral dosage form in such a way that the release in time of the substances may be effected in the best possible way according to pre-established schedules. Such a system should be adjustable according to the particular therapeutic characteristics of the active ingredient to be administered; should possess homogeneity characteristic such as to allow a correct dosage; and should maintain its characteristics in the selected vehicle for a long period of time even after the beginning of the treatment.

SUMMARY OF THE INVENTION

The present invention relates to a controlled release pharmaceutical dosage form, including: (a) microgranules of a pharmaceutical and excipients; (b) a plurality of polymeric lipidic and wax-like coatings applied to the microgranules, the coated microgranules having dimensions which allow suspension of the coated microgranules in a liquid administration vehicle; and (c) a liquid administration vehicle for the coated microgranules, the vehicle including an effective amount of the pharmaceutical in a form immediately available upon ingestion.

Another aspect of the present invention relates to a process for the preparation of the controlled release therapeutic system.

DETAILED DESCRIPTION OF THE INVENTION

The present inventors have now found that it is possible to obtain a controlled release therapeutic system for pharmaceutical liquid formulations having the above mentioned characteristics. Such a system includes microgranules containing the active ingredient (or pharmaceutical), particularly theophylline and its pharmaceutically acceptable salts, as well as a suitable excipient, coated by several alternated layers of suitably selected materials, in a vehicle containing an immediately available dose of the same active ingredient contained in the microgranules. Reference to theophylline is intended to include all of its pharmacologically acceptable salts.

In order to obtain a system having the required characteristics, it is necessary to obtain microgranules having a surface able to allow a uniform formation of film which can guarantee a constant release. For this reason, it is necessary that the active ingredient be first granulated and that the granules have a homogeneously smooth surface. Furthermore, in order to obtain the optimum suspension conditions and to limit the undesirable effect of the granules on the palate, it is necessary that, once the coating is completed, the final dimensions of the coated granules be between 50 and 600 mcm.

The microgranules so coated are mixed with suitable suspending and aromatizing agents and additives and stored in this way, constituting formulations which can be suspended in aqueous vehicles.

Alteratively, the coated microgranules may be dispersed and kept in a dispersion in the suitable liquid vehicle containing the suspending, aromatizing, and other agents, to obtain an immediately available dosage form. Both formulations have the property or remaining stable at room temperature for long periods which can be measured in several months.

It is also an object of the present invention to provide with the above mentioned formulations a prompt therapeutic response beside the protracted effect. Such prompt response is obtained through the contemporaneous presence in the dosage formulation, beside the controlled release forms, also of a predetermined quantity of the same active ingredient contained in the protracted release forms, a quantity which is mainly a function of the solubility of the active ingredient contained in the protracted release forms, a quantity which is mainly a function of the solubility of the active principle in the liquid selected as a vehicle. Such quantity of active ingredient may have been solubilized or introduced into the liquid form in an extemporaneous way. A dose of active ingredient is thus immediately available which will bridge the time gap needed by the controlled release forms to exert their action.

The present invention is applicable to a great variety of drugs having various characteristics and, particularly in the form of extemporaneous suspension, may be useful for such drugs which tend to be unstable when put in solution. Particularly interesting results may be obtained using theophylline as an active ingredient.

Theophylline has for a long time been considered the preferred drug for the treatment of acute and chronic bronchial constriction syndromes, and its use in therapy provides for frequent administrations during the day and for long periods of time, up to the disappearance of the symptoms.

A pharmaceutical formulation allowing the controlled release of theophylline has therefore the double advantage of maintaining the plasma levels in the range of therapeutic concentrations, and limiting the number of daily administrations, thus improving the compliance by the patient, and this in addition to be previously described advantages of the personally adapted dosage and of the practicality of use.

The present invention includes a controlled release therapeutic system dosable in liquid form comprising:

1) controlled release form of an active ingredient, particularly theophylline, having dimensions comprised between 50 and 500 mcm, able to easily remain in suspension in a liquid for long periods, including:

1.1) an active ingredient suitably transformed by means of excipient into a microgranular nucleus having well defined technological and morphological characteristics, which are essential to assure the reproduceability and the uniform distribution of the successive film layers;

1.2) a first coating in contact with the microgranular nucleus for the purpose of forming a barrier insensitive to pH variations. Such barrier, operating as a diffusion membrane, allows a regulation of the release of the drug contained in the nucleus and, at the same time, thanks to its intrinsic characteristics, makes it possible to maintain the preestablished dimension limits;

1.3) a series of successive coatings overlaying the first, which, while keeping the dimensions of the granules in the predetermined limits, constitute an alternation of layers of a hydrophilic and lipophilic character, which can be regulated in number and succession so as to be adapted to the pharmacological characteristics of the active ingredient employed. The therapeutic response is thus optimized and, at the same time, the complete dispersibility of the coated microgranules, at the moment of their suspension in the liquid vehicle is obtained.

2) A vehicle system for the mentioned controlled release form, alternatively includes:

2.1) a dry mixture of suspending agents, sweetening agents and of the controlled release forms described above at (1) to obtain a formulation which can be reconstituted at the moment of usage. Such formulation has rheological characteristics able to maintain in suspension the coated microgranules, alter their introduction in the aqueous solvent, and maintain the release characteristics unchanged for long periods of time;

2.2) a water solution of the above mentioned suspension and sweetening agents in which the controlled release forms described under (1) may be suspended and kept in optimal release conditions for long periods of time.

3) A predetermined quantity of the active ingredient added to the 2.1) mixture or dissolved into the 2.2) solution, for the purpose of supplying an immediately effective therapeutic dose at the moment of administration.

According to the present invention the present inventors have found that by wet kneading the active ingredient with excipient, it is possible to obtain granules having a high concentration of active ingredient and which have, in the final coating state, dimensions within 50 to 600 mcm (preferably 125– 300 mcm), a uniform, almost spherical surface, an apparent density comprised between 250–800 g/l) (preferably 500–600 g/l) and a very low friability. The present method may be applied to active ingredient differing both for their physical and chemical characteristics and for the therapeutic class to which they belong. The system is usable for the administration of a large variety of active ingredients, of acidic, basic or neutral character. The system may be applied to anti-inflammatory, anti-histaminic, diuretic, gastrokinetic, anti-asthmatic and other drugs. In particular, the system is suitable for the administration of theophylline.

The employed excipient may be selected among those commonly employed in wet kneading, such as for example, dibasic calcium phosphate lactose, microcrystalline cellulose, starch, talc, sugars, polyvinylpyrrolidone, polyvinylpyrrolidone-vinyl acetate copolymer, sodium phosphate, hydrogenated castor-oil, citric acid and tartaric acid. The kneading liquid may be water or a solvent miscible with water, as for example ethyl alcohol and other commonly used alcohols, or a water-alcohol mixture. According the invention, the granulate is then coated, in successive phases and according to known coating techniques, with films of different compositions. As an example, we list below the materials which may form the three different types of films employed.

First coating on the granule

The first coating may include a mixture in various ratios of a first component, consisting of cellulose derivatives such as hydroxy-propyl-cellulose phthalate, ethylcellulose, carboxyl-methyl-cellulose acetate, carboxyl-methyl-cellulose acetate butyrate and similar, or copolymers of esters of methacrylic and acrylic acid, methyl methacrylates and similar, with a second component consisting of hydrogenated or partially hydrogenated cottonsoy-, arachid-, castor-oil and similar, with the addition of a suitable plasticizing agent such as diethyl phthalate, mono glycerol acetate, polyethyleneglycol, or alkyl citrates.

Successive coating

Successive coatings may include a lipophilic component layer of fatty substances such as: mono, di-, or triglycerides of fatty acids having from 6 to 32 carbon atoms, carnauba wax, beeswax, candelilla wax, alcohols, fatty acids and the like.

A suitable hydrophilic component layer may be formed from substances having either gastroresistant characteristics or not, including: cellulose acetophthalate, hydroxypropylmethylcellulose phthalate, hydroxypropylcellulose, hydroxypropylmethyl cellulose, copolymers of methacrylic-, acrylic- and methylmetacrylic acid esters, and the like.

With the filming materials described above, the contemporaneous presence of plasticizers may be useful. As plasticizer one can employ, for instance, diethylphtalate, dibutylsebacate, triacetin, trialkyl nitrates, acetylated vegetable oils and glycerides, polyethylene glycols, propyleneglycol and others. The selection of the most suitable plasticizer depends on whether it is employed when operating in a water medium or with the aid of organic solvents or mixtures of them. As film solvents, in fact, one can use beside water, chlorinated solvents such as chloroform and others, and alcohols such as ethanol, methanol, isopropyl alcohol and others, as well as ketones such as acetone, methyl-ethylketone and others. The film coating consists of a first layer deposited on the granulate, followed by a succession of one or more superimposed layers "onion-wise", consisting of lipophilic and hydrophilic suitably alternated materials. Except for the need of alternating lipophilic and hydrophilic layers, the sequence and the number of layers are basically determined by the characteristics of the active ingredient to be administered and by the desired release characteristics. As examples, we list below some combinations of possible coating sequences: (a) ethylcellulose and hydrogenated castor oil followed by cellulose acetophthalate and plasticizer; (b) ethylcellulose and hydrogenated castor oil followed by cellulose acetophthalate and plasticizer, then alternating layers of waxes and cellulose acetophthalate, concluding with a cellulose acetophtalate and plasticizer layer as external layer; (c) ethylcellulose and hydrogenated castor oil followed by a layer consisting of a mixture of glyceryl monostearate, beeswax, cetyl and stearyl alcohol, followed by a layer of cellulose acetophthalate and plasticizer. If necessary, the alternating sequence of lipophilic and hydrophilic layers may be repeated several times; (d) ethylcellulose and hydrogenated castor oil followed by a layer consisting of a mixture of glyceryl monostearate, beeswax, cetyl and stearyl alcohol, alternating with layers of cellulose acetolphtalate and plasticizer; and (e) coating sequences similar to the ones described under points (a), (b) and (c) in which hydrogenated castor oil is substituted by diethylacetolphtalate or other plasticizers. In accordance with the present invention, the granulate coated according to the methods described may be then introduced into a vehicle in the following forms: (a) suspension ready to use; (b) solid mixture which can be suspended extemporaneously at the moment of usage.

In addition to the amount of coated microgranules containing the dose of controlled release active ingredient, the elements constituting the vehicle for form (a) are: (1)—a dose of active principle in solution, forming a readily absorbable fraction; (2) suspending and structural agents such as cellulose esters, microcrystalline cellulose, alginic acid derivatives, polyvinyl pyrroidone derivatives; (3) sugars, such as sucrose and sorbitol; (4) buffers such as citric acid and sodium citrate, glycine and hydrochloric acid, sodium and potassium phosphates; (5) preservatives and bacteriostatic agents such as p-hydroxybenzoic acid esters; (6) aromatizing and sweetening agents such as saccharine and others; and (7) water or mixtures of water and solvents such as glycols, alcohols, glycerin.

Form (b) on the other hand, consists of a mixture of the coated granulate containing the active ingredient in a controlled release dose and a mixture consisting of a fraction of the prompt release drug together with the excipient described in points (2) to (6), and which may be granulated according to conventional methods. In particular, the purpose of the pharmaceutical form in the extemporaneous suspension (b), is to make it possible to use a vehicle also for those active ingredients which, in a aqueous vehicle, might present problems of chemical stability in the times foreseen for the therapeutic use. Set forth below are methods, tables and examples intended to better illustrate the invention, showing its advantages and applicability, without, however, constituting a limitation of the same. Even if in such examples reference is made to some known drugs only, it is evident that the present invention may be applied to a large number of active ingredients both of a similar or different structure.

EXAMPLE 1

A. Preparation of the microgranulate

The active principle and the excipient are introduced in a kneading vessel, the powders are mixed for a time sufficient to obtain a homogeneous mixture and then the kneading liquid is added.

The liquid is distributed in the homogeneous powder mix by spraying through a nozzle of a diameter which may vary between 0.6 and 2 mm, depending both on the spraying pressure which may vary between 0.6 and 6 Bar, and the type of wetting solution employed.

By varying the dimension of the nozzle one can obtain a more or less subdivided nebulization, so as to adjust the liquid distribution during the wetting step according to requirements. The wetting liquid may be brought to the diffusion nozzle by means of a peristaltic pump, or a similar system, with a flux which may vary between 20 and 80 ml/min, depending on the liquid selected, and at any rate in such a way as to obtain a uniform distribution of the liquid in the powder mixture. At the end of the wetting, the granulate is made into spheres maintaining the mixing of the mass for a time between 5 and 20 minutes, depending on the operative conditions and on the materials employed in the preceding steps. Once the formation of the spheres is terminated, the product is dried in a static oven or on a fluid bed according to known techniques, resulting in a granulate ready for film coating having a high content of active ingredient, a size between 50 and 500 mcm and a spheroidal form which does not present sharp or discontinuous surfaces. The powder fraction, below 50 mcm, and the coarse fraction, above 500 mcm, are separated and pulverized with the aid of a mill, and used again in successive operations. We report herein below some compositions for 100 g granulate obtained with the described technique:

| Components | Weight (g) |
| --- | --- |
| a) | |
| Theophylline | 80 |
| Bibasic bihydrated calcium phosphate | 10 |
| Talc | 5 |
| Polivinylpyrrolidone vinyl acetate | 5 |
| b) | |
| Hydrated, micronized theophylline | 24 |
| Microcrystalline cellulose | 15 |
| Corn starch | 15 |
| Lactose | 39 |
| Polyvinylpirrolidone | 7 |
| c) | |
| Micronized ketorolac | 2 |
| Microcrystalline cellulose | 15 |
| Corn starch | 15 |
| Lactose | 58 |
| Polyvinylpirrolidone | 10 |
| d) | |
| Micronized hydrated theophylline | 80 |
| Hydrogenated castor-oil | 10 |
| Talc | 5 |
| Polyvinylpirrolidone vinylacetate | 5 |
| e) | |
| Anhydrous micronized theophylline | 80 |
| monohydrated citric acid | 9,6 |
| Bihydrated bibasic sodium phosphate | 0,4 |
| Talc | 2,5 |
| Polyvinylpirrolidone vinyl acetate | 7,5 |

B. Film coating of the microgranulate

For applying the film coating one can employ known techniques, such as conventional pans, fluid bed systems and other similar methods.

The coating material may be applied by dissolving the film forming materials into organic solvents or using aqueous dispersions of the materials, or even by applying directly the materials in the molten state.

We report hereinbelow some examples of the coating layer composition for 100 ml of film forming solution. a) first film forming coating in contact with the granule:

| Components | |
| --- | --- |
| Ethylcellulose | 1 g |
| Hydrogenated castor oil | 1 g |
| Chloroform | 65 ml |
| Ethanol | 35 ml |
| or: | |
| Ethylcellulose | 4 g |
| Diethylphthalate | 1 g |
| Chloroform | 65 ml |
| 95% ethanol | 35 ml |
| or: | |
| Ethylcellulose | 4 g |
| Hydrogenated castor oil | 1 g |
| Chloroform | 65 ml |
| 95% ethanol | 35 ml |
| b) hydrophilic film coating | |
| Cellulose acetophthalate | 5 g |
| Diethylphtalate | 1,25 g |
| Acetone | 75 ml |
| Isopropanol | 25 ml |
| c) lipophilic film coating | |
| Glyceryl monostearate | 9 g |

| Components | |
| --- | --- |
| White beeswax | 0,8 g |
| Cetyl alcohol | 0,1 g |
| Stearyl alcohol | 0,1 g |
| Chloroform | 90 ml |
| Methanol | 10 ml |

Film forming method

The granulate spheres are introduced in a Glatt fluid bed apparatus provided with a 1.2 mm nozzle and the apparatus is preheated to 35° C. The (a) coating solution is sprayed feeding the nozzle with a peristaltic pump, keeping a constant flux and nebulizing by means of air injected at a pressure of 2 Bar. Once the coating with solution (a) is terminated, coating of successive alternating layers using solutions (b) and (c) is performed in a similar way. If required by the desired release and active ingredient characteristics, the filming with materials of solutions b) and c) may be repeated several times. In general, the last coating layer consists of solution (b). When the filming of the last layer is completed, the coated granulate is dried, for example keeping it in the Glatt at 40° C. for at least 30 minutes, after which the coated product is ready to be dispersed in the liquid vehicle.

C. Preparation of a ready liquid formulation

In a portion of the water necessary for the preparation, the preservatives are dissolved and the structure forming material dispersed until swollen, then the active ingredient constituting the ready dose and the excipient and sweetening agents required are added. After adding the buffer and the release controlled granulate containing the active ingredient, the aromatizing substance is added and the whole mixture is brought to the desired volume. Described below is an example of a composition for preparing 100 ml of a dosage liquid corresponding to 3 g of anhydrous theophylline.

| Components | Dose |
| --- | --- |
| Theophylline (dose ready to use) | 0,6 g |
| Coated granulate (retard dose) corresponding to anhydrous theophylline | 2,4 g |
| Microgranular cellulose | 2,0 g |
| Sodium carboxymethylcellulose | 0,26 g |
| Hydroxyethylcellulose | 0,05 g |
| Sucrose | 14,00 g |
| Sodium saccarinate | 0,10 g |
| Methyl p-hydroxybenzoate | 0,15 g |
| Propyl p-hydroxybenzoate | 0,05 g |
| Glycocoll | 0,73 g |
| 1 N hydrochloric acid | 1,2 ml |
| Mint-artichoke aroma | 0,5 g |
| Water | q.s. to 100 ml |

EXAMPLE 2

Preparation of a liquid formulation to be reconstituted. We describe an example of a compositions for 100 ml of extemporaneous suspension:

| Components | Dose (g) |
| --- | --- |
| Theophylline (dose ready to use) | 0,60 |
| Coated granulate (retard dose) corresponding to anhydrous theophylline | 2,10 |
| Sodium alginate | 1,00 |
| Sodium citrate | 0,22 |
| Citric acid | 0,41 |

| Components | Dose (g) |
|---|---|
| Sodium saccarinate | 0,20 |
| Sodium methyl p-hydroxybenzoate | 0,15 |
| Sodium propyl p-hydroxybenzoate | 0,05 |
| Orange aroma powder | 0,10 |
| Sucrose | 14,00 |

The retard granulate prepared as described in example 1 and coated with successive film layers according to the method described at point B. is mixed in a suitable ratio with a granulate constituting the release portion. This last granulate is prepared by kneading in water a mixture consisting of theophylline, sucrose, sodium alginate, sodium saccarinate, sodium citrate, citric acid, sodium methyl- and propyl-p-hydroxybenzoate. After granulating on a 0.300 mm mesh sieve, the product is dried to a constant humidity content and then is admixed with the powdered aroma.

Release control

The release control is performed using powder apparatus II (paddle) of the United States Pharmacopeia XXI Ed., operating at 50 rpm using 900 ml of a phosphate buffer at pH 7.4 having the following composition:

| Bihydrated bibasic sodium phosphate | 14,40 g |
|---|---|
| Bihydrated monobasic sodium phosphate | 2,96 g |
| Demineralized water | q.s. to 1000 ml |

The determination of the released active ingredient is performed spectrophotometrically or through HPLC according to known methods.

The release tests are carried out on microgranules with film coverings which differ in type and composition, and which are employed in such quantity so as not to reach the saturation limits of the dissolution medium for the various assayed active ingredients (sink condition).

Various types of film coatings are prepared for the dissolution test in vitro.

The following dissolution table will evidence the advantages of the invention with respect to possible coating alternatives.

TABLE 1

Dissolution of granules having dimensions of 125–250 mcm with multilayer coating and differing one from the other only because of the thickness of the first coating layer.

| Time (hrs) | A | B | C | D | E |
|---|---|---|---|---|---|
| | | | (dissolution %) | | |
| 1 | 95 | 1,7 | 8,3 | 8,3 | 10,8 |
| 2 | 100 | 2,5 | 10,8 | 12,5 | 17,9 |
| 4 | | 4,2 | 14,2 | 20,0 | 29,3 |
| 6 | | 5,8 | 16,7 | 25,0 | 34,7 |
| 8 | | 8,3 | 19,2 | 29,2 | 40,4 |

Thickness of the first coating layer=A: not coated, B: 1013 mcm, C: 9–10 mcm, D: 8–8 mcm, E: 5–6 mcm. The higher the thickness of the first layer, the lower the drug release.

TABLE 2

Dissolution comparison between granules with two layer coating of the same materials. In these cases the microgranules were not coated with the first ethylcellulose-hydrogenated castor oil layer. (F): coating with a wax layer and with a layer of cellulose acetophthalate (CAP). (G): coating with several wax and CAP alternating layers.

| Time (hrs) | F | G |
|---|---|---|
| | (dissolution %) | |
| 1 | 4,2 | 2,3 |
| 2 | 16,6 | 7,4 |
| 4 | 58,3 | 33,3 |
| 6 | 96,0 | 63,0 |
| 8 | 100 | 84,0 |

Because of the reduced dimensions of the particles to be coated, in case (F) in order to obtain release values comparable to case (G), one must distribute a high amount of waxes (50–60% of the total granule weight) thus going beyond the predetermined dimension limits for the coated microgranule.

TABLE 3

Comparison of the dissolution between a complete multilayer coating (E) and a multilayer coating containing only waxes and CAP (G) and no first ethylcellulose-hydrogenated castor oil layer.

| Time (hrs) | E | G |
|---|---|---|
| | (dissolution %) | |
| 1 | 10,8 | 2,3 |
| 2 | 17,9 | 7,4 |
| 4 | 29,3 | 33,3 |
| 6 | 34,7 | 63,0 |
| 8 | 40,4 | 84,0 |

The advantage of the complete multiple coating (E) consists in keeping reduced granule dimensions while maintaining the efficacy in delaying the release of the active ingredient, notwithstanding the high surface area of the particles.

TABLE 4

Comparison of the dissolution of multilayer coatings differing only because of the number of layers after the first. Description of the layers:

a: ethylcellulose-hydrogenated castor oil mixture; b: CAP; and c: waxes.

Formulations and coatings:

(H)=a/b, (I)=a/b/c/b, (L)=a/b/c/b/c/b.

| Time (hrs) | H | I | L |
|---|---|---|---|
| | | (dissolution %) | |
| 1 | 10,0 | 14,0 | 8,0 |
| 2 | 12,0 | 17,0 | 12,0 |
| 4 | 14,0 | 23,0 | 17,0 |
| 6 | 18,0 | 27,5 | 22,0 |
| 8 | 21,0 | 31,0 | 27,0 |

It is evident that by alternating hydrophilic and lipophilic layers, one can advantageously change the rate of dissolution, making it more constant with time.

TABLE 5

Dissolution of multi-layer coating microgranules containing naproxene (M), ketorolac-trometamine (0) and theophylline (Q) in comparison with the dissolution of non-coated granules containing respectively the same active ingredients (N. P. R).

| Time (hrs) | M | N | O | P | Q | R |
|---|---|---|---|---|---|---|
| | | | (dissolution %) | | | |
| 1 | 26,0 | 85,0 | 29,0 | 95,0 | 26,5 | 96,0 |
| 2 | 36,0 | 95,0 | 36,5 | 100 | 31,2 | 100 |
| 4 | 48,0 | 100 | 49,0 | | 45,7 | |
| 6 | 57,0 | | 60,0 | | 54,8 | |
| 8 | 65,0 | | 72,0 | | 61,9 | |

The table shows the possibility of employing the multilayer film forming for substances with different physicochemical characteristics.

Release tests were also carried out on film covered microgranules suspended in a suitable aromatized vehicle containing 20% theophylline as ready dose, in an amount such as not to reach the saturation limits of the dissolution medium (sink condition).

For the dissolution tests in vitro, various formulation types were prepared taking mainly into account two parameters: the composition of the microgranulates and the type of coating. In Table 6 some examples are reported. In all of them the first film coating which regulates the release of the active ingredient, is followed by five alternating hydrophilic and lipophilic coating layers.

TABLE 6

Dissolution of suspensions containing granules having dimensions between 125 and 250 mcm with a multilayer coating, and differing one from the other because of the characteristics of the microgranulate or the ones of the first coating layer.

| Time (hrs) | A | S | T | U | V |
|---|---|---|---|---|---|
| | | | (dissolution %) | | |
| 1 | 95,00 | 35,59 | 34,41 | 39,49 | 32,01 |
| 2 | 100 | 42,64 | 42,33 | 46,75 | 49,50 |
| 4 | | 53,29 | 52,77 | 53,98 | 59,89 |
| 6 | | 61,05 | 60,68 | 58,83 | 67,41 |
| 8 | | 66,68 | 65,85 | 62,33 | 72,70 |

A=microgranulate without coating; S=microgranulate consisting of a mixture of theophylline, calcium phosphate, talc, polyvinylpyrrolidone vinylacetate, coated with a first layer consisting of ethyl cellulose and diethylphthalate and with a series of 5 alternating lipophilic and hydrophilic layers; T=microgranulate consisting of a mixture of theophylline, hydrogenated castor oil, talc, polyvinylpyrrolidone vinylacetate, coated with a first layer consisting of ethyl cellulose and diethylphthalate and with a series of 5 alternating lipophilic and hydrophilic layers; U=microgranulate consisting of a mixture of theophylline, calcium phosphate, talc, polyvinylpyrrolidone vinylacetate, coated with a first layer consisting of ethyl cellulose and hydrogenated castor oil, and with a series of 5 alternating lipophilic and hydrophilic layers; and V=microgranulate consisting of a mixture of theophylline, citric acid, sodium phosphate, talc, polyvinylpyrrolidone vinylacetate, coated with a first layer consisting of ethyl cellulose and diethylphthalate, and with a series of 5 alternating lipophilic and hydrophilic layers. From the data of Table 8 it is evident how the coating of the granules can allow to adjust the release of an active ingredient.

Stability

The stability controls were performed by evaluating the behavior with time of the formulations prepared according to the description in example 1 (liquid formulation ready to use) and in example 2 (formulation to be reconstituted in liquid form). The stability with time, of the release characteristics of the drug, was verified by dissolution tests performed according to what previously described in the paragraph relating to the release control.

TABLE 7

Stability at room temperature of liquid formulations ready to use (W: initial. X: after six months) and reconstituted (Y: initial, Z: after six months), both containing theophylline as an active ingredient.

| Time (hrs) | W | X | Y | Z |
|---|---|---|---|---|
| | | (dissolution %) | | |
| 0 | 19,4 | 25,6 | 21,0 | 21,6 |
| 1 | 26,5 | 36,1 | 29,5 | 30,0 |
| 2 | 31,2 | 41,7 | 30,0 | 34,2 |
| 4 | 45,7 | 54,5 | 31,0 | 40,8 |
| 6 | 54,9 | 62,2 | 35,5 | 47,5 |
| 8 | 58,7 | 66,2 | 45,1 | 48,5 |

Relative Bioavailability Control

The relative bioavailability of the theophylline formulations described in Table 6 was verified by a pharmacokinetic study performed on Beagle dogs. Dogs of both sexes, of weight comprised between 12 and 14 Kg, were treated in two crossover design studies with a single oral dose of liquid theophylline formulations containing each 300 mg of active ingredient. A controlled release theophylline formulation in tablets (THEO-DUR®300) was used as reference standard. Blood specimens were taken at 0, 0.6, 1.0, 1.6, 2, 3, 4, 6, 8, 11, 24, 28 and 32 hours after administration and were then analyzed to determine, by HPLC method, the plasma theophylline concentrations. The bioavailability parameters are summarized in tables 8–9. For the formulations and the standard are reported the mean values relative to: area under the plasma concentration/time curves between 0 and 32 hours ($AUC_0$-32), time for reaching the highest concentration ($T=_{max}$ and the highest concentration reached ($C=_{max}$), S. E. is the standard error and CV represents the variation coefficient on the average.

TABLE 8

Bioavailability parameters of two controlled release theophylline formulations described in table 6, in comparison with a THEO-DUR® 300 formulation.

| | THEO-DUR[R] | S | T |
|---|---|---|---|
| | $AUC_{0-32}$ | (h · mcg/ml) | |
| average | 216,01 | 184,49 | 223,71 |
| ± S.E. | 3,36 | 3,60 | 9,63 |
| CV (%) | 2,70 | 3,38 | 7,45 |
| | $T =_{max}$ (hours) | | |
| average | 4,33 | 4,67 | 4,33 |
| ± S.E. | 0,72 | 0,54 | 0,72 |
| CV (%) | 28,78 | 20,20 | 28,78 |
| | $C_{max}$ (mcg/ml) | | |
| average | 20,18 | 15,01 | 20,38 |
| ± S.E. | 2,29 | 0,71 | 2,75 |
| CV (%) | 19,64 | 8,24 | 23,36 |

TABLE 9

Bioavailability parameters of two controlled release theophylline formulations described in table 6, in comparison with a THEO-DUR® 300 formulation.

|  | THEO-DUR$^R$ | U | V |
| --- | --- | --- | --- |
|  | $AUC_{0-32}$ | (h · mcg/ml) | |
| average | 286,74 | 242,67 | 252,17 |
| ± S.E. | 3,80 | 21,45 | 8,40 |
| CV (%) | 2,30 | 15,31 | 5,77 |
|  | $T_{max}$ (hours) | | |
| average | 6,67 | 5,67 | 5,33 |
| ± S.E. | 1,91 | 1,19 | 1,44 |
| CV (%) | 44,50 | 36,26 | 46,77 |
|  | $C_{max}$ (mcg/ml) | | |
| average | 17,72 | 16,79 | 17,63 |
| ± S.E. | 1,55 | 0,22 | 1,29 |
| CV (%) | 15,16 | 2,22 | 12,68 |

The data in the tables show that is possible, by a suitable variation in the composition of the formulations to obtain a good bioavailability of the active ingredient, which is at any rate comparable to the one of a solid formulation of the same active ingredient having well-known therapeutic characteristics.

What is claimed is:

1. A controlled release pharmaceutical dosage form comprising microgranules comprising a pharmaceutical and excipients and comprising a homogeneously smooth surface with at least three coatings deposited thereon, said coatings comprising:

a pH insensitive coating constituting a barrier operating as a diffusion membrane and allowing regulation of the release of said pharmaceutical;

a second coating applied on said pH-insensitive coating and comprising a member selected from the group consisting of a polymeric, hydrophilic coating and a hydrophobic coating;

a third coating applied on the second coating and comprising a member selected from the group consisting of a polymeric hydrophilic coating and a hydrophobic coating with the proviso that when said second coating comprises a polymeric hydrophilic coating said third coating comprises a hydrophobic coating and vice versa;

said microgranules with all the plural coatings thereon having dimensions which allow stable suspension of the plural coated microgranules in a liquid administration vehicle.

2. The dosage form of claim 1 further comprising additional polymeric hydrophilic coatings alternating with additional hydrophobic coatings.

3. The dosage form of claim 2 wherein said plural coated microgranules have dimensions between 50 and 600 μm.

* * * * *